(12) United States Patent
Horita et al.

(10) Patent No.: US 10,735,534 B2
(45) Date of Patent: Aug. 4, 2020

(54) INFORMATION PROCESSING APPARATUS

(71) Applicant: FUJI XEROX CO., LTD., Tokyo (JP)

(72) Inventors: Ryoji Horita, Kanagawa (JP);
Katsunori Kawano, Kanagawa (JP);
Akinori Komura, Kanagawa (JP);
Minoru Mitsui, Kanagawa (JP)

(73) Assignee: FUJI XEROX CO., LTD., Tokyo (JP)

( * ) Notice: Subject to any disclaimer, the term of this patent is extended or adjusted under 35 U.S.C. 154(b) by 84 days.

(21) Appl. No.: 15/993,601

(22) Filed: May 31, 2018

(65) Prior Publication Data
US 2019/0173967 A1 Jun. 6, 2019

(30) Foreign Application Priority Data
Dec. 5, 2017 (JP) .................. 2017-233632

(51) Int. Cl.
*H04L 29/12* (2006.01)
*H04L 29/06* (2006.01)
*H04L 29/08* (2006.01)
*A61B 5/16* (2006.01)
*G16H 50/00* (2018.01)
*A61B 5/0205* (2006.01)
*G06F 3/06* (2006.01)
*H04Q 9/00* (2006.01)

(52) U.S. Cl.
CPC .......... *H04L 67/22* (2013.01); *A61B 5/02055* (2013.01); *A61B 5/165* (2013.01); *G16H 50/00* (2018.01); *H04L 65/403* (2013.01); *H04L 65/80* (2013.01); *H04Q 9/00* (2013.01)

(58) Field of Classification Search
USPC ........ 709/223, 228, 232, 230, 239, 250, 204
See application file for complete search history.

(56) References Cited

U.S. PATENT DOCUMENTS

| 2003/0061231 | A1* | 3/2003 | Lovegren | G06Q 10/10 |
| 2009/0049165 | A1* | 2/2009 | Long | H04L 41/046 |
| | | | | 709/223 |
| 2009/0322854 | A1* | 12/2009 | Ellner | H04N 7/147 |
| | | | | 348/14.08 |
| 2011/0070572 | A1* | 3/2011 | Miller | G09B 7/02 |
| | | | | 434/322 |
| 2012/0253875 | A1* | 10/2012 | Harsh | G06Q 10/0631 |
| | | | | 705/7.15 |
| 2012/0253887 | A1* | 10/2012 | Lum | G06Q 30/02 |
| | | | | 705/7.32 |
| 2014/0359012 | A1* | 12/2014 | Watanabe | H04L 65/403 |
| | | | | 709/204 |
| 2016/0308920 | A1* | 10/2016 | Brunsch | H04L 67/24 |

FOREIGN PATENT DOCUMENTS

| JP | 2005198086 | 7/2005 |
| JP | 2009163431 | 7/2009 |
| JP | 2016091490 | 5/2016 |

* cited by examiner

*Primary Examiner* — Jude Jean Gilles
(74) *Attorney, Agent, or Firm* — JCIPRNET

(57) ABSTRACT

An information processing apparatus includes a specifying unit that specifies an activity degree of each of a plural participants based on biometric information obtained from a living body of each of the plural participants participating in a gathering, an evaluation unit that evaluates each of the plural participants based on the specified activity degree, a selection unit that selects one or more of the plural participants based on an evaluation of the evaluation unit, and a requesting unit that requires an opinion on the gathering from the selected participant.

20 Claims, 6 Drawing Sheets

FIG. 5A
| PARTICIPANT ID | UNIQUE INFORMATION | DESTINATION INFORMATION |
|---|---|---|
| U01 | ... | ... |
| U02 | ... | ... |
| ... | ... | ... |
121
FIG. 5B
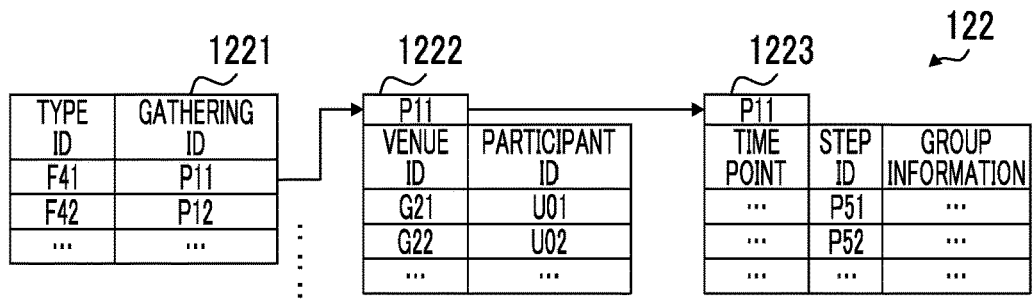
FIG. 5C
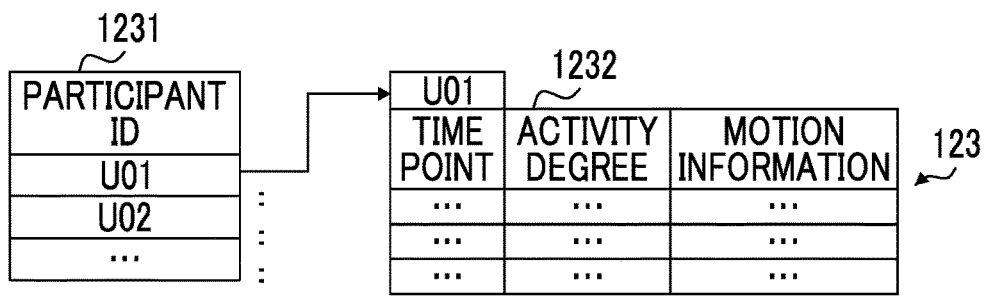
FIG. 5D
| CONDITION | LEVEL | FORM | WEIGHTING FACTOR |
|---|---|---|---|
| ... | ... | ... | ... |
| ... | ... | ... | ... |
| ... | ... | ... | ... |
124

INFORMATION PROCESSING APPARATUS

CROSS-REFERENCE TO RELATED APPLICATIONS

This application is based on and claims priority under 35 USC 119 from Japanese Patent Application No. 2017-233632 filed Dec. 5, 2017.

BACKGROUND

(i) Technical Field

The present invention relates to an information processing apparatus.

(ii) Related Art

Creativity and productivity are required for gatherings such as a conference. A technology of using biometric information obtained from the living body of each participant for managing a gathering in order to improve creativity and the like of the gathering has been developed.

SUMMARY

According to an aspect of the invention, there is provided an information processing apparatus which includes a specifying unit that specifies an activity degree of each of plural participants based on biometric information obtained from a living body of each of the plural participants participating in a gathering, an evaluation unit that evaluates each of the plural participants based on the specified activity degree, a selection unit that selects one or more of the plural participants based on an evaluation of the evaluation unit, and a requesting unit that requests an opinion on the gathering from the selected participant.

BRIEF DESCRIPTION OF THE DRAWINGS

Exemplary embodiment (s) of the present invention will be described in detail based on the following figures, wherein:

FIGS. 5A to 5D are diagrams illustrating a database stored in a storage unit 12;

DETAILED DESCRIPTION

Exemplary Embodiment

Overall Configuration of Information Processing System

Figure 1:
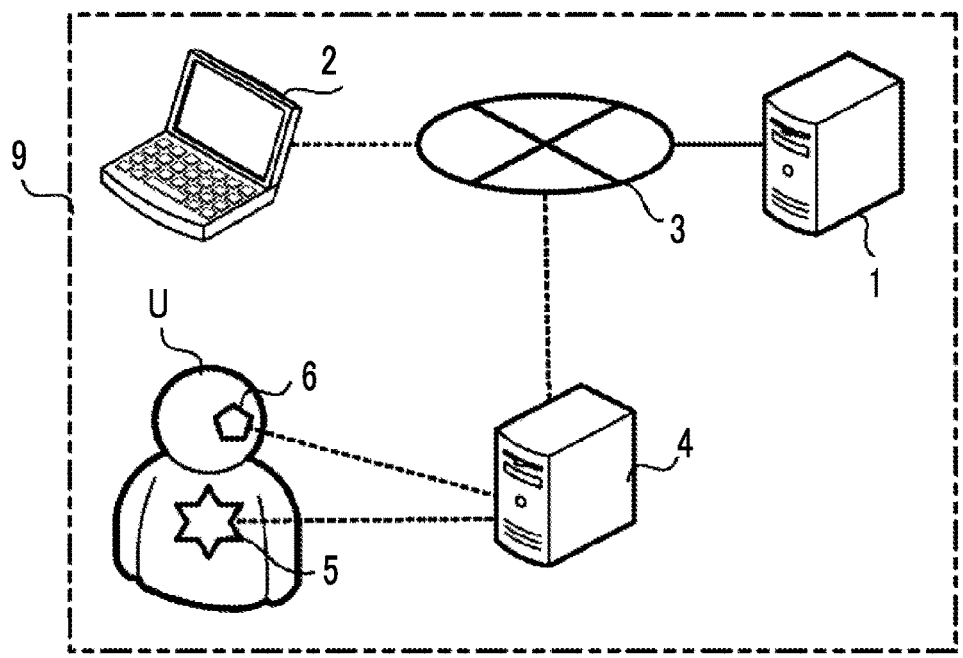
FIG. 1 is a diagram illustrating a configuration of an information processing system 9 according to an exemplary embodiment.

FIG. 1 is a diagram illustrating an information processing system 9 according to an exemplary embodiment. The information processing system 9 includes a server device 1, a terminal 2, a collection device 4, and a communication line 3 which is connected to the server device, the terminal, and the collection device so as to enable communication with each other. The information processing system 9 includes a measurement device 5 and an observation device 6. In the information processing system 9 illustrated in FIG. 1, the measurement device 5 and the observation device 6 are connected to the collection device 4. The information processing system 9 may include an imaging device such as a camera or a sound collection device such as a microphone, in order to recognize figures or voices of participants U in a gathering. The imaging device performs imaging of the figure of a participant U. The sound collection device collects the voice of a participant U or environmental sounds generated in the surroundings.

The information processing system 9 may include plural server devices 1 and plural communication lines 3. In the exemplary embodiment, the communication line 3 links plural venues. The terminal 2, the collection device 4, the measurement device 5, and the observation device 6 are provided in each venue. However, for simple descriptions, one terminal, one collection device, one measurement device, and one observation device are illustrated in FIG. 1. Although plural participants U are provided as targets in the information processing system 9, one person is illustrated in FIG. 1.

The server device 1 is an information processing apparatus that records activity degrees and motion information of all participants U or participants U who have got permission in advance, selects a participant U who is to perform an evaluation after the gathering ends, and requests an opinion from the selected participant U, in a gathering held with plural venues linked.

Here, "the gathering" means that plural venues are linked by a communication line and participants U in each of the venues perform communication with each other in a form of, for example, dialogues and gestures. For example, a conference, a meeting, a debate, a study group, a social meeting, and a massive multiplayer game are provided as "the gathering".

The terminal 2 is a terminal device used by a participant U in a gathering and is a terminal device used for transmitting an opinion to the server device 1 as a response to a request. In the example, one terminal 2 is assigned to each participant U.

The communication line 3 is a line that connects the server device 1 with the terminal 2 and the collection device 4 to enable communication with each other. For example, the Internet is provided.

For example, at least one collection device 4 is provided in each venue and the collection device collects pieces of information of participants U who are in the venue and participates in a gathering. The collection device 4 is connected to the measurement device 5 and the observation device 6 so as to collect information provided by each of the measurement device and the observation device and to transmit the collected information to the server device 1.

In FIG. 1, the collection device 4 is connected to one measurement device 5 and one observation device 6. However, the collection device may be connected to plural measurement devices or plural observation devices.

The measurement device 5 is a device that measures information such as an electrocardiographic waveform, a pulse wave, a heartbeat, and a breathing rate of a participant U, which is obtained from the living body of the participant (referred to as biometric information below). The measurement device 5 includes plural electrodes which are brought into contact with the skin of a participant U, for example. The measurement device measures an electrocardiographic waveform by measuring impedance between the electrodes.

The participant U may conditionally permit a use for handling of the own biometric information measured by the measurement device 5. In this case, for example, a counterpart for which the measured biometric information is provided may be limited only to the participant U, a facilitator of the gathering, or the like. Limitations as follows may be provided. That is, the participant U does not provide the measured biometric information itself but provides the measured biometric information by expressing the measured biometric information with a prepared character string, the color of an icon, the type of the icon, and the like.

The observation device 6 is a device that observes information regarding a motion (motion information), such as the amount of a motion (motion amount) of the participant U, a direction of the motion, a portion of the participant U, which is moving, and the like, by using an acceleration sensor mounted on, for example, the head of the participant U or the arms and legs thereof. The observation device 6 may observe the motion amount of each moving portion. For example, in a case where the position of the heart of a participant moves with movement of the body thereof, observation may be performed in a manner that a component along the gravity is separated among moving directions and the separated component is used as the motion amount.

Configuration of Collection Device

Figure 2:
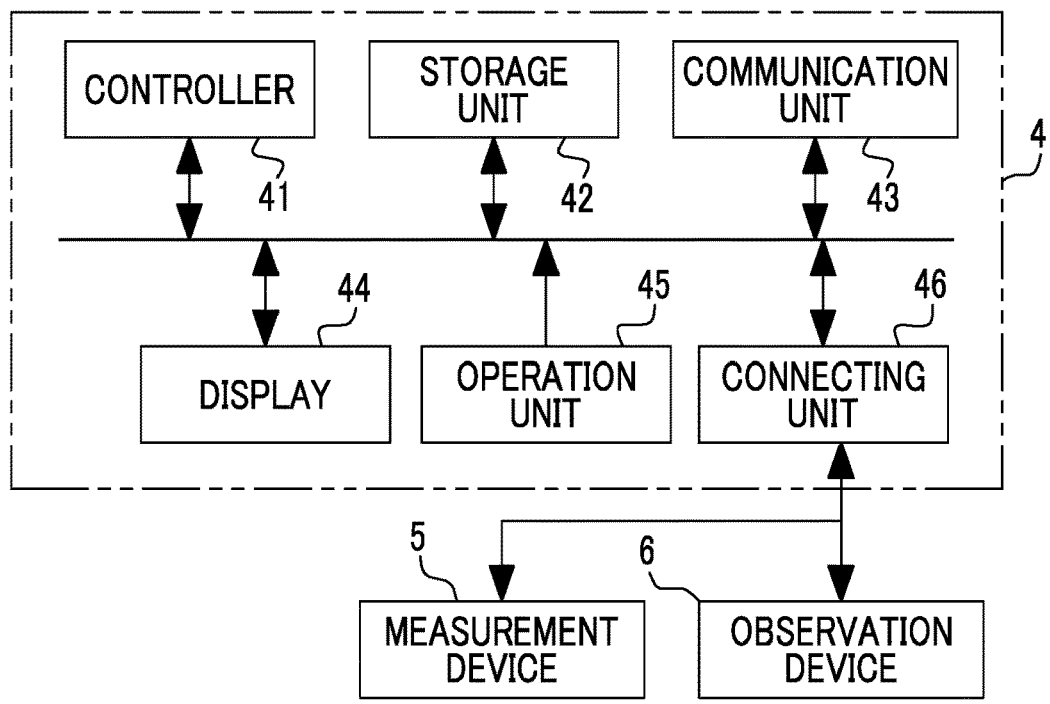
FIG. 2 is a diagram illustrating an example of a configuration of a collection device 4.

FIG. 2 is a diagram illustrating an example of a configuration of the collection device 4. The collection device 4 includes a controller 41, a storage unit 42, a communication unit 43, a display 44, an operation unit 45, and a connecting unit 46.

The controller 41 includes a central processing unit (CPU), a read only memory (ROM), and a random access memory (RAM). The controller controls the units of the collection device 4 by the CPU reading and executing a computer program (simply referred to as a program below) stored in the ROM and the storage unit 42.

The communication unit 43 is a communication circuit connected to the communication line 3 in a wired or wireless manner. The collection device 4 transmits and receives information to and from the server device 1 connected to the communication line 3, by the communication unit 43.

The operation unit 45 includes operation components such as operation buttons, a keyboard, and a touch panel for inputting various instructions. The operation unit receives an operation by a user and transmits a signal corresponding to operation contents, to the controller 41.

The display 44 includes a display screen such as a liquid crystal display. The display displays an image under a control of the controller 41. A transparent touch panel of the operation unit 45 may be disposed on the display screen to overlap the display screen. The collection device 4 may not include the operation unit 45 or the display 44.

The storage unit 42 is a large capacity storage section such as a solid state drive and a hard disk drive. The storage unit stores various programs, pieces of data, and the like which are to be read out by the CPU of the controller 41.

The connecting unit 46 is an interface for performing connection to a device that supplies various types of information. The connecting unit 46 illustrated in FIG. 2 is connected to the measurement device 5 and the observation device 6. The connecting unit 46 may be connected to an imaging device or a sound collection device (not illustrated) and may supply data generated by the imaging device or the sound collection device to the controller 41.

The connecting unit 46 collects biometric information such as an electrocardiographic waveform of a participant U, from the measurement device 5 and collects motion information of the participant U from the observation device 6.

Various types of information acquired through the connecting unit 46 are supplied to the controller 41 and are associated with a time point and the participant U under a control of the controller 41. The resultant is transmitted to the server device 1 through the communication unit 43 and the communication line 3.

Configuration of Terminal

Figure 3:
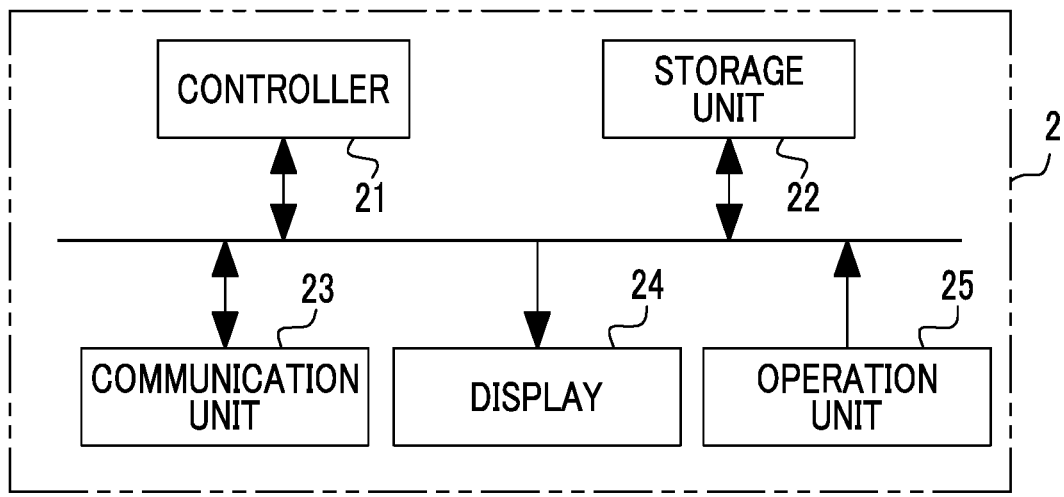
FIG. 3 is a diagram illustrating an example of a configuration of a terminal 2.

FIG. 3 is a diagram illustrating an example of a configuration of the terminal 2. The terminal 2 includes a controller 21, a storage unit 22, a communication unit 23, a display 24, and an operation unit 25.

The controller 21 includes a CPU, a ROM, and a RAM. The controller 21 controls the units of the terminal 2 by the CPU reading and executing a program stored in the ROM and the storage unit 22.

The communication unit 23 is a communication circuit connected to the communication line 3 in a wired or wireless manner. The terminal 2 transmits and receives information to and from the server device 1 connected to the communication line 3, by the communication unit 23.

The operation unit 25 includes operation components such as operation buttons, a keyboard, and a touch panel for inputting various instructions. The operation unit receives an operation by a user and transmits a signal corresponding to operation contents, to the controller 21.

The display 24 includes a display screen such as a liquid crystal display. The display displays an image under a control of the controller 21. A transparent touch panel of the operation unit 25 may be disposed on the display screen to overlap the display screen.

The display 24 may include a mechanism of transmitting information by using a sense of a user other than the sense of sight, in addition to or instead of the above-described display screen. For example, the display 24 may include a speaker that outputs sound represented by sound data, and a vibration generator that comes into contact with the body of the user and transmits vibration.

The storage unit 22 is a large capacity storage section such as a solid state drive and a hard disk drive. The storage unit stores various programs, pieces of data, and the like which are to be read out by the CPU of the controller 21.

Configuration of Server Device

Figure 4:
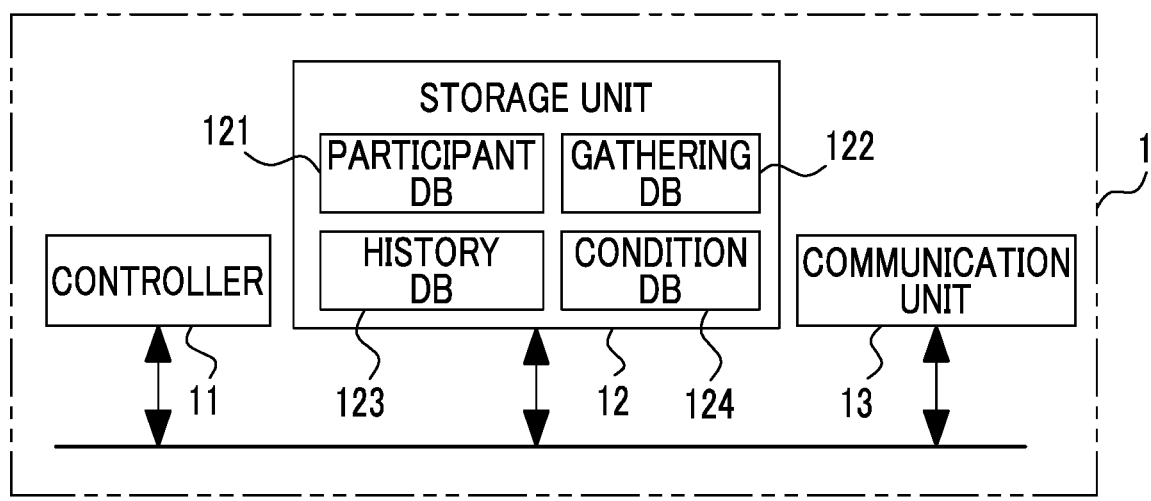
FIG. 4 is a diagram illustrating a configuration of a server device 1.

FIG. 4 is a diagram illustrating a configuration of the server device 1. The server device 1 includes a controller 11, a storage unit 12, and a communication unit 13.

The controller 11 includes a CPU, a ROM, and a RAM. The controller 11 controls the units of the server device 1 by the CPU reading and executing a program stored in the ROM and the storage unit 12.

The communication unit 13 is a communication circuit connected to the communication line 3 in a wired or wireless manner. The server device 1 transmits and receives information to and from the terminal 2 and the collection device 4 which are connected to the communication line 3, by the communication unit 13.

The storage unit 12 is a large capacity storage section such as a hard disk drive. The storage unit stores various programs, pieces of data, and the like which are to be read out by the CPU of the controller 11.

The storage unit 12 stores a participant DB 121, a gathering DB 122, a history DB 123, and a condition DB 124.

FIGS. 5A to 5D are diagrams illustrating a database stored in the storage unit 12. The participant DB 121 is a database in which information of a participant participating in a gathering is stored. The participant DB 121 illustrated in FIG. 5A stores a participant ID as identification information for identifying a participant, unique information as information unique to the participant, and destination information indicating a destination of a message sent to the participant, in association with each other.

The unique information associated with the participant is, for example, information used for normalizing the activity degree or the motion amount of the participant. "Normalizing" the activity degree or the motion amount, which is described here, means processing of expressing the activity degree or the motion amount with, for example, a ratio using the maximum value, the minimum value, or the like of the activity degree or the motion amount which has been previously specified for the participant. Thus, an individual difference between the numerical values is canceled out.

The destination information associated with the participant indicates, for example, an email address, a telephone number, or the like of the participant.

The gathering DB 122 is a database in which information on a participant participating in a gathering is stored. The gathering DB 122 illustrated in FIG. 5B includes a gathering list 1221, a venue list 1222, and a step list 1223.

The gathering list 1221 is a list of a gathering ID which is identification information of a gathering. As illustrated in FIG. 5B, a type ID indicating the type of the gathering may be associated in the gathering list 1221, for each gathering.

The type of the gathering is a type classified by the setup, the procedure, the method, or the like used in the gathering. For example, a gathering proceeded in a certain manner incorporates a process in which each participant speaks frankly with their self-introductions at the beginning. A meeting held in a certain setup incorporates a step in which a speaker finishes a brief explanation of the agenda, and then two participants sitting adjacent to each other form a pair and exchange opinions on the explanation for 10 minutes. The type ID is used for identifying a gathering by characteristic setup and the like relating to the progress of the gathering.

In the venue list 1222, a participant ID indicating a participant in a gathering and a venue ID as identification information of a venue in which the participant actually moves are stored in association with each gathering ID.

In the step list 1223, a time point of starting a step performed in a gathering, a step ID as identification information of a step, and group information which is information on grouping in a case where participants perform a joint work such as opinion exchange are stored in association with each gathering ID.

The history DB 123 is a database in which history indicating how the activity degree and the motion information of a participant in a gathering has changed is stored. The history DB 123 illustrated in FIG. 5C includes a participant list 1231 and a history list 1232.

The participant list 1231 is a list of a participant ID. The history list 1232 is a list in which changes of the activity degree and the motion information of a participant identified by the corresponding participant ID, with time, are stored for each participant ID described in the participant list 1231. In the history list 1232, the activity degree and the motion information of a participant, which has been measured, observed, or specified at a time point are stored in association with each time point. That is, in the history list 1232 illustrated in FIG. 5C, history of a set of the activity degree specified for a participant and motion information of the participant when the activity degree has been specified is stored.

The condition DB 124 is a database in which a condition relating to an evaluation of a participant, a level indicating the stage of the evaluation of a participant satisfying the condition, and a form when an opinion is requested from a participant having the level are stored in association with each other. "The level" indicating the stage of the evaluation of a participant is used in dividing an evaluation level of the participant in stages.

"The form" when an opinion is requested means, for example, a timing of requesting the opinion, contents of a message for requesting the opinion, an email or a short message, a web form, a method of sending a message for request, and a remuneration when a participant responds to the request.

Since the level and the form are associated with each other, an opinion is required in a form in accordance with importance or contribution of a participant indicated by the level, for a gathering. For example, it may be as follows. A guide of filling a questionnaire is delivered to a participant who acts centrally in a gathering, by an email with a label indicating that the guide is an important matter, within 5 minutes after the gathering ends. In addition, a guide of filling a questionnaire is delivered to a participant who assists other participants although not acting centrally in the gathering, by a short mail at the next day after the gathering.

As illustrated in FIG. 5D, in the condition DB 124, a weighting factor indicating the degree of weighting which is given to the contents of a response may be associated with each level of a participant when the response indicating the required opinion is obtained from the participant and the response is aggregated.

Functional Configuration of Server Device

Figure 6:
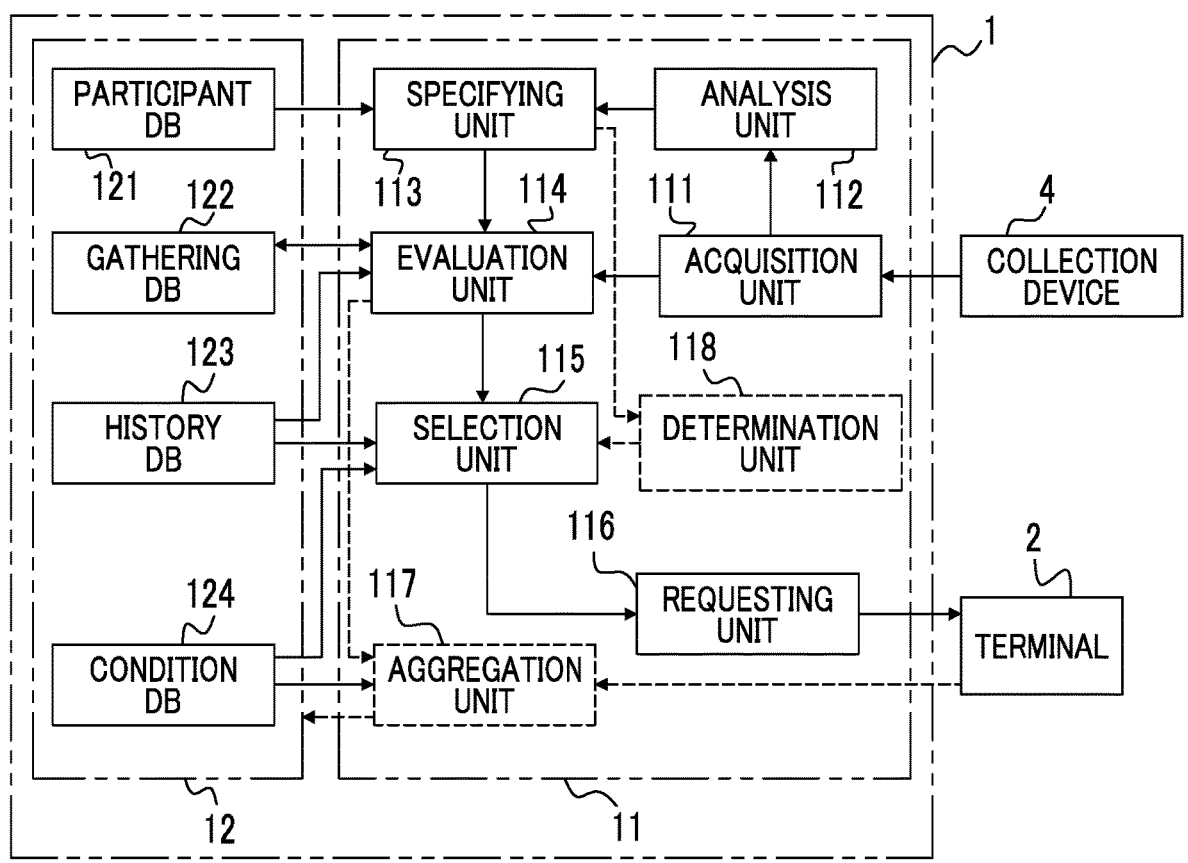
FIG. 6 is a diagram illustrating a functional configuration of the server device 1.

FIG. 6 is a diagram illustrating a functional configuration of the server device 1. The controller 11 of the server device 1 functions as an acquisition unit 111, an analysis unit 112, a specifying unit 113, an evaluation unit 114, a selection unit 115, and a requesting unit 116, by reading and executing a program stored in the storage unit 12. The controller 11 may function as an aggregation unit 117 and a determination unit 118 illustrated with broken lines in FIG. 6. In FIG. 6, illustrations of the communication line 3 and the communication unit 13 are omitted.

The acquisition unit 111 acquires biometric information of a participant U and motion information of the participant U from the collection device 4. Here, the biometric information indicates an electrocardiographic waveform which has been measured by electrodes of the measurement device 5 mounted on the participant U, has been collected by the collection device 4, and then has been transmitted to the server device 1. The motion information of the participant U is information which has been observed by the observation device 6, has been collected by the collection device 4, and then has been transmitted to the server device 1. The motion information includes the motion amount of the participant.

The analysis unit 112 performs analysis for specifying the activity degree of the participant U based on the acquired biometric information. For example, the analysis unit 112 performs frequency analysis of the electrocardiographic waveform as the acquired biometric information so as to obtain frequency components of heart rate fluctuation, such as a very low frequency (VLF) component, a low frequency (LF) component, and a high frequency (HF) component.

Fast Fourier transform, Fourier series expansion with uneven intervals, wavelet transform, and the like are used in the analysis performed by the analysis unit 112. The analysis unit 112 may convert the time series of the electrocardiographic waveform by using, for example, cubic spline interpolation such that the R-R intervals are equally spaced. In a case where the acquisition unit 111 acquires biometric information (for example, a pulse wave, a heartbeat, and a breathing rate) of the participant other than the electrocardiographic waveform, the analysis unit 112 may analyze the biometric information.

LF is a word indicating a low frequency. A variable wave (blood pressure fluctuation) which is called the Mayer wave and uses a blood pressure change having a period of about 10 seconds, as a signal source, or the total amount (integrated value) of the power spectrum in the frequency area is indicated by LF. The frequency area of LF is, for example, equal to or greater than 0.05 Hz and smaller than 0.15 Hz.

HF is a word indicating a high frequency. A variable wave (respiratory fluctuation) which uses a blood pressure change having a period of about 3 seconds to 4 seconds, as a signal source, or the total amount (integrated value) of the power spectrum in the frequency area is indicated by HF. The frequency area of HF is, for example, equal to or greater than 0.15 Hz and smaller than 0.40 Hz.

The autonomic nerves are classified into sympathetic nerves and parasympathetic nerves. In a case where the sympathetic nerves are excited, noradrenalin is released. The β receptor of a cell in the sinoatrial node receives the noradrenaline, and thereby a series of chemical reactions starts in the cell and the heart rate increases.

In a case where the parasympathetic nerves are excited, acetylcholine is released. The muscarinic receptor of the cell of the sinoatrial node receives the acetylcholine, and thereby a chemical reaction starts in the cell and the heart rate falls.

All of the chemical reactions of the sympathetic nerves and parasympathetic nerves have a mechanism of a reuse loop of chemical substances. Materials used in the reactions are recycled and return to the original states. The reaction time until the materials return to the original states is different between the sympathetic nerves and the parasympathetic nerves. Thus, the response speed for the transmitted signal is different.

For example, the chemical reaction of the sympathetic nerves, which involves noradrenalin and the β receptor has difficulty in responding to a change having a period which is shorter than a period of about 6 seconds. Therefore, in the sympathetic nerves, transmitting respiratory fluctuation having a period of about 3 seconds to 4 seconds is difficult.

The chemical reaction of the parasympathetic nerves, which involves acetylcholine and the muscarinic receptor proceeds faster than the chemical reaction of the sympathetic nerves. Thus, response to fluctuation having a period of about 1 second is also possible. Accordingly, the parasympathetic nerve transmits the respiratory fluctuation.

The blood pressure fluctuation has a period of about 10 seconds. Thus, all of the parasympathetic nerves and the sympathetic nerves may transmit the blood pressure fluctuation.

When the sympathetic nerve is suppressed, and the parasympathetic nerve is accelerated (tense), both the blood pressure fluctuation and the respiratory fluctuation are reflected in the heart rate fluctuation by the parasympathetic nerve. On the contrary, when the sympathetic nerve is accelerated, and the parasympathetic nerve is suppressed, the blood pressure fluctuation is reflected in the heart rate fluctuation by the sympathetic nerve, but the respiratory fluctuation is not reflected.

For the above reasons, the HF component reflecting the respiratory fluctuation appears in the heart rate fluctuation only in a case where the parasympathetic nerve is activated (excited). The LF component reflecting the blood pressure fluctuation also appears in the heart rate fluctuation in a case where any of the sympathetic nerve and the parasympathetic nerve is activated. Therefore, when the HF component is relatively large, it is understood that the parasympathetic nerve tends to be tense. When the LF component is relatively large, it is understood that the sympathetic nerve tends to be tense. For example, a value (LF/HF) obtained by dividing the LF component by the HF component represents the activity degree of the sympathetic nerve and is handled as an index of the strength of stress.

The specifying unit 113 specifies the activity degree of the participant U based on results of the analysis performed by the analysis unit 112. That is, the specifying unit 113 specifies the activity degree of a participant, which is analyzed based on biometric information obtained from the living body of the participant participating in a gathering.

The activity degree of the participant U is an index indicating how active the participant U acts. The activity degree of the participant U indicates the concentration degree of the participant U, the depth of understanding, activeness of a mental activity, and the like. The activity degree is derived as a function of a value (for example, LF component and HF component which are described above) which is obtained by the specifying unit 113 from the frequency analysis of an electrocardiographic waveform, which has been performed by the analysis unit 112. Examples of the activity degree include the sum of the LF component and the HF component. The activity degree may be normalized for each participant with the specifying unit 113 referring to the participant DB 121. In the following descriptions, a numerical value obtained by normalization with the minimum value of 0 and the maximum value of 1 is used as the activity degree.

The evaluation unit 114 specifies plural participants participating in a gathering as a target of determination, with reference to the gathering DB 122. The evaluation unit 114 reads history of the activity degree from the history DB 123, evaluates each of the specified participants based on the activity degree thereof, and then stores results obtained by the evaluation, for example, in the storage unit 12.

In a case of evaluating a participant, the evaluation unit 114 may use motion information read from the history DB 123 in addition to the activity degree of the participant. That is, the evaluation unit 114 evaluates each of the plural participants participating in the gathering, based on the motion information and the activity degree.

For example, it is known that the activity degree obtained from biometric information is influenced depending on how much the position of the heart of the living body moves in the direction along the gravity. For example, the evaluation unit 114 calculates a component along the gravity among directions in which the position of the heart of a participant moves, based on the above knowledge. In a case where it is determined that "the participant stands up", the evaluation unit 114 may evaluate the participant by correcting the activity degree depending on the calculated component.

The evaluation unit 114 may evaluate each of the plural participants participating in a gathering, based on the frequency of the activity degree being equal to or greater than a threshold value in the gathering. Thus, it is easy to distinguish a case where the activity degree is accidentally increased by an influence of a motion of a participant, an environment, or the like, from a case where the activity degree is increased by an influence of activation of a mental activity, which occurs by participation in the gathering.

The evaluation unit 114 may evaluate each of the participants by using the activity degree specified when the participant participating in the gathering and the activity degree specified when not participating in the gathering. In this case, for example, the evaluation unit 114 calculates a statistical value such as the maximum value, the minimum value, the average value, the median value, variance, and standard deviation, based on history of the activity degree which has been previously specified for each of the participants. The evaluation unit 114 evaluates the participant by comparing the calculated statistical value and the activity degree specified in the gathering. Thus, for example, a participant having an activity degree which increases due to an influence of the gathering in which the participant participates is highly evaluated.

The evaluation unit 114 may evaluate each of the participants by using the statistical value which has been calculated from the activity degrees of plural participants participating in the gathering and the activity degree of each of the participants. In this case, for example, the evaluation unit 114 calculates a statistical value such as the maximum value, the minimum value, the average value, the median value, variance, and standard deviation, based on the activity degrees of all of the above-described participants participating in the gathering. The evaluation unit 114 evaluates each of the participants by comparing the calculated statistical value and the activity degree of each of the participants. Thus, the plural participants participating in the gathering is relatively evaluated based on a comparison to all participants in the gathering.

The evaluation unit 114 may evaluate a participant, for example, by sorting plural participants participating in a gathering, in order of the activity degree. In addition, the evaluation unit 114 may classify participants into plural categories by using a threshold value determined based on various statistical values such as the arithmetic mean, the geometric mean, and the median of activity degrees of the participants, and may evaluate the participants. In a case where a predetermined threshold value is provided, the evaluation unit 114 may classify participants based on a determination of whether or not the participant has an activity degree which is equal to or greater than the threshold value and may evaluate the participants.

The determination unit 118 determines a gathering in which an opinion is to be requested from a participant, among plural gatherings, by determination of whether or not activity degrees of plural participants participating in the gathering satisfy a predetermined condition. That is, the determination unit 118 determines a gathering in which activity degrees of plural participants participating in the gathering satisfy a predetermined condition, among plural gatherings, as an examination target.

As the above-described condition, various conditions may be provided. For example, the determination unit 118 may determine a gathering based on similarity between activity degrees of plural participants. "The similarity" described here means the degree of association with a time change. That is, in this case, the determination unit 118 determines a gathering based on the extent to which the activity degrees of the plural participants have changed with association while the gathering proceeds.

For example, when participants, which correspond to a predetermined percentage (for example, 80%), in a gathering have activity degrees which increase at a common timing, when the participants have activity degrees which decrease at a common timing, or when shapes of graphs obtained when the activity degrees are time-differentiated are similar to each other in a predetermined range, it is considered that the participants in the gathering influence each other and sympathize with each other. At this time, the determination unit 118 determines that creativity of the gathering is high and determines a gathering as the examination target (gathering for which an opinion is to be requested).

In a gathering, in a case where a step of forming a pair by two participants adjacent to each other and causing the two participants to communicate with each other for an agenda, the determination unit 118 may determine a gathering by determination of whether or not the activity degrees of the pair are synchronized with each other in a predetermined range. In this case, the determination unit 118 may determine each step included in the gathering, as the examination target.

For example, in a case where over half of participants in a gathering, which have activity degrees being equal to or greater than a threshold value three times or greater within a predetermined time difference is specified, the determination unit 118 may determine the gathering as the examination target.

The selection unit 115 selects one or more participants among plural participants, based on the evaluation of the evaluation unit 114 with reference to the condition DB 124.

The selection unit 115 may select one or more participants among plural participants participating in a gathering, for each gathering. In a case where a gathering proceeds through plural steps, the selection unit may select a participant for each of the steps.

For example, the selection unit 115 averages evaluation values of participants, which have been calculated based on activity degrees, for each gathering. The selection unit selects a participant having an activity degree which is equal to or greater than the obtained average value. The selection unit 115 compares activity degrees of plural participants to a predetermined threshold value (for example, 0.6) and selects a participant having an activity degree which is equal to or greater than the threshold value.

The level described in the condition DB 124 may be assigned to the selected participant in accordance with the evaluation. That is, the selection unit 115 may classify each of plural participants participating in a gathering into any of plural levels, in accordance with the evaluation by the evaluation unit 114. The selection unit may perform selection.

In a case where the controller 11 is caused to function as the above-described determination unit 118, the selection unit 115 may select a participant from participants in the determined gathering and may not select a participant from participants in a gathering which has not been determined.

The requesting unit 116 requests an opinion on a gathering from the participant selected by the selection unit 115.

In a case where the selection unit 115 classifies each participant into any of the plural levels in accordance with an evaluation, the requesting unit 116 may request an opinion on the gathering from the participant in a form depending on the level into which the participant is classified.

In this case, the requesting unit 116 requests the above-described opinion from the participant by transmitting a message to the terminal 2 in a form associated with the level of the selected participant.

The message is transmitted in a manner of an email, a short message, or the like. An electronic file for describing an opinion may be attached to the message or a uniform resource identifier (URI) of a web site including an input form for describing an opinion may be described in the message.

Regarding an opinion required to a participant, an opinion on one item may be required or an opinion on plural items may be required, for each gathering.

Examples of the plural items for a gathering include various kinds of information for characterizing the gathering as follows: the date, a time, the number of participants, a place, an agenda, and an objective; a slide, wording, or picture on which strong impression remains; and a method, a procedure, and a type of gathering.

Examples of the plural items for a gathering include various kinds of information indicating subjectivity of a participant for degrees of various items as follows: the degree of creativity for the participant himself, the degree of creativity of the gathering, the degree of satisfaction, the degree of accomplishment, reliability to the chairman, the degree of understanding of the agenda, and the progress of forming a crowd. For example, the kinds of information are represented in order scale such as three levels of "good, normal, and bad" or five levels of "very good, good, normal, bad, very bad".

The plural items for a gathering may be information indicating the number related to the result of the gathering, such as the number of discovered themes, the number of specified themes, and the number of activities spread and fixed. The kinds of information are represented, for example, in an interval scale or a proportional scale.

The aggregation unit 117 receives a response of a participant to a request, from the terminal 2 of the participant to which the requesting unit 116 requests an opinion. The aggregation unit aggregates received responses. Thus, opinions of participants participating in a gathering are collected, and thus, for example, the percentage of the participants who are satisfied and have feelings of achievement in the gathering among participants participating in the gathering can be recognized. Characteristics of a gathering evaluated to have high creativity by a relatively large number of participants are grasped by aggregating the responses.

The aggregation unit 117 may aggregate the response of a participant with a weight based on the evaluation of the participant by the evaluation unit 114. For example, the aggregation unit 117 multiplies the 5-levels of evaluation for the gathering, which is included in the response of the participant, by the numerical value indicating the evaluation of the participant. The aggregation unit 117 may set a value obtained by dividing the total of the calculated values by the number of responses, as an evaluation of the gathering. Thus, as a participant participates actively in a gathering and does not influence other participants, an aggregation result in which the subjectivity of the participant is emphasized more is obtained.

The aggregation unit 117 may aggregate responses for each type of gathering. Thus, the type of a gathering obtaining a high evaluation by opinions of participants is specified. Accordingly, in a case where a new gathering is planned, a gathering having the above type is adopted. For example, in a case where knowledge of a gathering group in which participants introduce themselves at the beginning being evaluated higher than a gathering group in which participants do not introduce themselves is obtained, the planner may plan a gathering in which a step of performing self-introduction at the beginning is provided.

In a case where the controller 11 is caused to function as the above-described determination unit 118, a participant is selected for each gathering determined by the determination unit 118 and an opinion is required to the selected participant. Thus, in this case, the aggregation unit 117 aggregates responses of participants participating in a gathering, for each gathering determined by the determination unit 118.

Operation of Server Device

Figure 7:
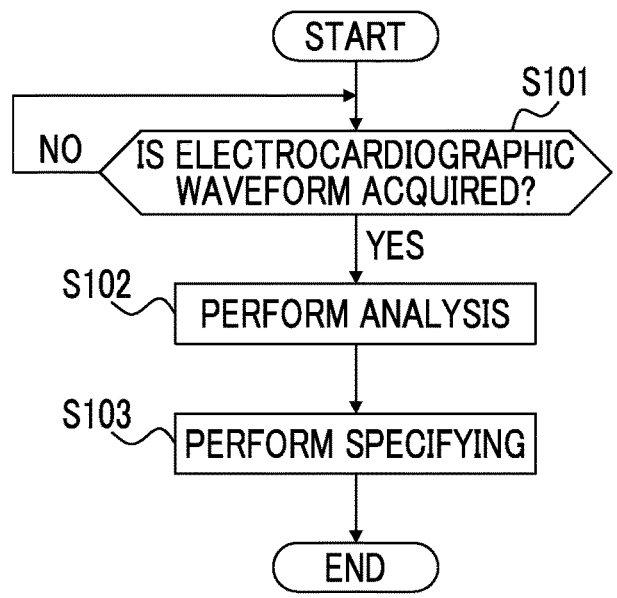
FIG. 7 is a flowchart illustrating a flow of an operation of the server device 1 specifying an activity degree.

FIG. 7 is a flowchart illustrating a flow of an operation in which the server device 1 specifies the activity degree. The controller 11 of the server device 1 determines whether or not an electrocardiographic waveform (example of biometric information) of a participant is acquired from the collection device 4 (Step S101). The controller 11 continues this determination during a period (NO in Step S101) of determining that the electrocardiographic waveform is not acquired. In a case where it is determined that the electrocardiographic waveform of the participant has been acquired (YES in Step S101), the controller 11 analyzes the electrocardiographic waveform (Step S102). The controller 11 specifies the activity degree of the participant based on an analysis result obtained by analyzing the electrocardiographic waveform (Step S103).

Figure 8:
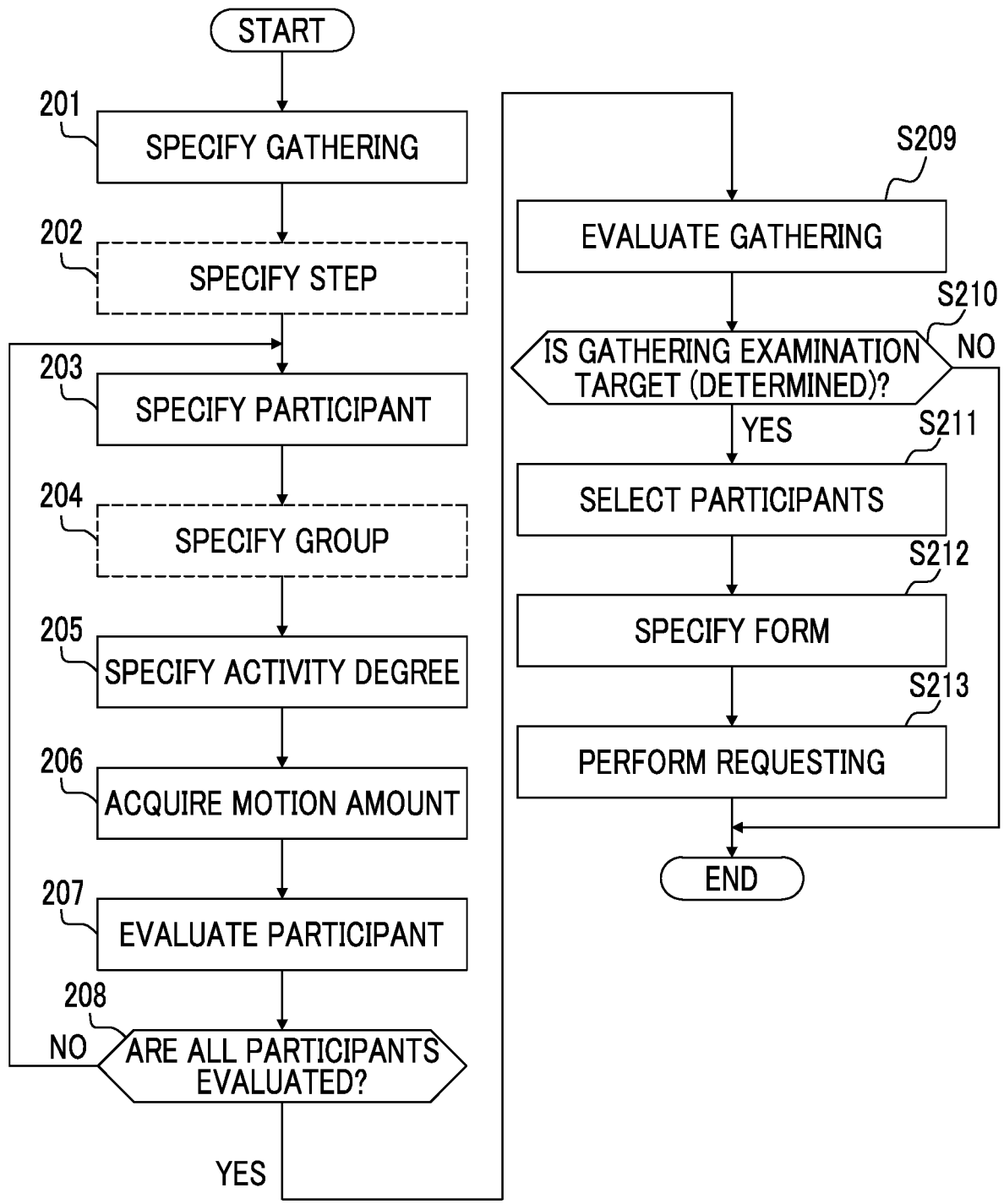
FIG. 8 is a flowchart illustrating a flow of an operation of the server device 1 requesting an opinion from a participant in a gathering.

FIG. 8 is a flowchart illustrating a flow of an operation in which the server device 1 requests an opinion from a participant in a gathering. The controller 11 of the server device 1 specifies a gathering (Step S201) and specifies any step included in the gathering, with reference to, for example, the gathering DB 122 (Step S202).

The controller 11 may not specify any step included in the gathering, after specifying the gathering. In this case, the step list 1223 may not be included in the gathering DB 122 stored in the storage unit 12 of the server device 1.

The controller 11 reads group information associated with the specified step, from the gathering DB 122. The controller 11 specifies a participant participating in the specified step (Step S203) and specifies a group to which the specified participant belongs (Step S204).

In a case where the step is not specified in above-described Step S202, the controller 11 may not specify the group to which the specified participant belongs.

The controller 11 specifies the activity degree of the above-described participant (Step S205), acquires the motion amount of the participant (Step S206), and evaluates the participant based on the specified activity degree and the acquired motion amount (Step S207). In a case where a rule of evaluating participants for each group is provided, for example, the controller 11 may evaluate the participant, based on determination of whether or not similarity between the activity degree of the above-described participant and the activity degrees of other participants belonging to the same group as that of the above participant is equal to or greater than a threshold value.

The controller 11 determines whether or not all participants in the gathering specified in Step S201 or in the step specified in Step S202 are evaluated (Step S208). In a case where it is determined that all of the participants are not evaluated (NO in Step S208), the controller 11 causes the process to return to Step S203.

In a case where it is determined that all of the participants are evaluated (YES in Step S208), the controller 11 evaluates the gathering based on evaluations of all of the participants (Step S209). The controller 11 determines the gathering by determining whether or not the gathering is a gathering for which an opinion is to be requested, that is, whether or not the gathering is the examination target (Step S210).

In a case where it is determined that the evaluated gathering is not the examination target (NO in Step S210), the controller 11 ends the process. In a case where it is determined that the evaluated gathering is the examination target (YES in Step S210), the controller 11 selects one or more participants among plural participants participating in the evaluated gathering, based on the evaluations of the participants (Step S211).

The controller 11 specifies a form in a case of requesting an opinion from the selected participant, with reference to the condition DB 124 (Step S212). The controller 11 requests the opinion from the above-described participant in the specified form (Step S213).

Figure 9:
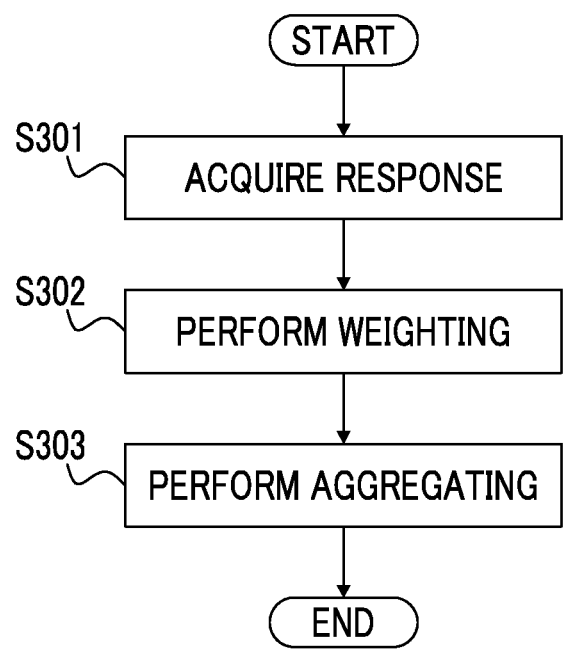
FIG. 9 is a flowchart illustrating a flow of an operation of the server device 1 aggregating a response of the participant.

FIG. 9 is a flowchart illustrating a flow of an operation in which the server device 1 aggregates a response of a participant. The controller 11 of the server device 1 acquires a response of a participant to the request in Step S213 (Step S301). The controller 11 specifies a weighting factor depending on the level of the participant who has transmitted the response and weights the contents of the response (Step S302). The controller 11 aggregates the weighted contents of the response (Step S303).

With the above-described operations, the server device selects a participant who actively participates in a gathering among plural participants participating in the gathering by using the activity degree based on biometric information obtained from the living body of the participant. Since the server device 1 requests opinions from the selected participants, an opinion of a participant who does not actively participate in the gathering is excluded from the above-described response.

The server device 1 aggregates an opinion of a participant who actively participates in the gathering and evaluates the gathering based on the results obtained by the aggregation. Thus, an evaluation considering both an objective evaluation, for example, biometric information of the participant and a subjective evaluation, for example, the opinion of the participant is made for the gathering.

In a case where the gathering is evaluated for each type, the type of a gathering having high creativity is estimated as a result obtained by aggregation of the server device 1. Thus, in a case where a new gathering is planned, the result of the estimation is used.

For example, with the information processing system 9, knowledge that creativity of a gathering is improved by performing a process in which each participant speaks frankly with their self-introductions at the beginning of the gathering in which 4 persons participate for 2 hours is accumulated.

Modification Example

Although the above descriptions are made for the exemplary embodiment, details of the exemplary embodiment may be modified as follows. The following modification examples may be combined.

Modification Example 1

In the above-described exemplary embodiment, the evaluation unit 114 corrects the activity degree based on the motion information and evaluates a participant. However, the evaluation unit may correct the activity degree based on environmental information indicating the surrounding environment of the participant, in addition to or instead of the motion information. For example, the environmental information means information obtained from the surrounding environment of the participant, such as the temperature or humidity of a venue in which the participant is located, a wind direction or an air volume, smell, and vibration. In this case, the observation device 6 may observe the above-described environmental information.

Events indicating the environmental information and the motion information are not observation events (psychogenic events) caused by the psychological state of the participant, but are observation events (such as an environment or a motion) caused by a state other than the psychological state. Thus, the above events are also defined as non-psychogenic events.

Modification Example 2

In the above-described exemplary embodiment, the controller 11 functions as the acquisition unit 111, the analysis unit 112, the specifying unit 113, the evaluation unit 114, the selection unit 115, the requesting unit 116, the aggregation unit 117, and the determination unit 118, by reading and executing the program stored in the storage unit 12. However, any of the functions may be performed in the terminal 2 or the collection device 4.

For example, in a case where the controller 41 acquires biometric information from the measurement device 5, the controller 41 of the collection device 4 realizes the function corresponding to the above-described acquisition unit 111.

The controller 41 of the collection device 4 may perform analysis for specifying the activity degree of a participant based on the acquired biometric information. That is, the controller 41 may realize the function corresponding to the above-described analysis unit 112. In this case, the controller 41 may transmit information indicating a result obtained by the analysis to the server device 1. The controller 11 of the server device 1 may specify the activity degree of the participant based on the received information.

In the information processing system 9, the terminal 2 may perform the function of the collection device 4 together. In the above-described exemplary embodiment, although the communication line 3 links plural venues, the information processing system 9 may be applied to a gathering held in one venue. In this case, the server device 1 may perform the functions of the terminal 2 and the collection device 4 and the communication line 3 may not be provided.

Modification Example 3

The program executed by the controller 11 of the server device 1 may be provided in a state of being stored in a recording medium readable by a computer device, such as a magnetic recording medium (for example, a magnetic tape and a magnetic disk), an optical recording medium (for example, an optical disk), a magneto-optical recording medium, and a semiconductor memory. The program may be downloaded via a communication line such as the Internet. Various devices other than the CPU may be applied as a control section exemplified by the above-described controller 11. For example, a dedicated processor or the like is used.

The foregoing description of the exemplary embodiments of the present invention has been provided for the purposes of illustration and description. It is not intended to be exhaustive or to limit the invention to the precise forms disclosed. Obviously, many modifications and variations will be apparent to practitioners skilled in the art. The embodiments were chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

What is claimed is:

1. An information processing apparatus comprising:
   a specifying unit that specifies an activity degree of each of a plurality of participants based on biometric information obtained from a living body of each of the plurality of participants participating in a gathering;
   an evaluation unit that evaluates each of the plurality of participants based on the specified activity degree;
   a selection unit that selects one or more of the plurality of participants based on an evaluation of the evaluation unit; and
   a requesting unit that requests an opinion on the gathering from the selected participant.

2. The information processing apparatus according to claim 1, further comprising:
   an acquisition unit that acquires motion information indicating a motion of each of the plurality of participants,
   wherein the evaluation unit evaluates each of the plurality of participants based on the motion information and the activity degree.

3. The information processing apparatus according to claim 1,
   wherein the evaluation unit evaluates each of the plurality of participants based on a frequency of the activity degree becoming a threshold value or greater in the gathering.

4. The information processing apparatus according to claim 2,
   wherein the evaluation unit evaluates each of the plurality of participants based on a frequency of the activity degree becoming a threshold value or greater in the gathering.

5. The information processing apparatus according to claim 1,
   wherein the evaluation unit evaluates each of the participants by using the activity degree specified when participating in the gathering and the activity degree specified when not participating in the gathering.

6. The information processing apparatus according to claim 2,
   wherein the evaluation unit evaluates each of the participants by using the activity degree specified when participating in the gathering and the activity degree specified when not participating in the gathering.

7. The information processing apparatus according to claim 3,
   wherein the evaluation unit evaluates each of the participants by using the activity degree specified when participating in the gathering and the activity degree specified when not participating in the gathering.

8. The information processing apparatus according to claim 4,
   wherein the evaluation unit evaluates each of the participants by using the activity degree specified when participating in the gathering and the activity degree specified when not participating in the gathering.

9. The information processing apparatus according to claim 1,
   wherein the evaluation unit evaluates each of the participants based on a statistical value calculated from activity degrees of the plurality of participants and the activity degree of each of the participants.

10. The information processing apparatus according to claim 2,
    wherein the evaluation unit evaluates each of the participants based on a statistical value calculated from activity degrees of the plurality of participants and the activity degree of each of the participants.

11. The information processing apparatus according to claim 3,
    wherein the evaluation unit evaluates each of the participants based on a statistical value calculated from activity degrees of the plurality of participants and the activity degree of each of the participants.

12. The information processing apparatus according to claim 4,
    wherein the evaluation unit evaluates each of the participants based on a statistical value calculated from activity degrees of the plurality of participants and the activity degree of each of the participants.

13. The information processing apparatus according to claim 5,
    wherein the evaluation unit evaluates each of the participants based on a statistical value calculated from activity degrees of the plurality of participants and the activity degree of each of the participants.

14. The information processing apparatus according to claim 1,
    wherein the selection unit performs selection by classifying the plurality of participants into a plurality of levels based on the evaluation, and
    the requesting unit requests the opinion from the participant in a form in accordance with the level to which the participant belongs.

15. The information processing apparatus according to claim 1,
    wherein the gathering proceeds through a plurality of steps, and
    the selection unit selects the participant for each of the steps of the gathering.

16. The information processing apparatus according to claim 1, further comprising:
    an aggregation unit that aggregates a response of the participant to a request of the requesting unit.

17. The information processing apparatus according to claim 16,
    wherein the aggregation unit aggregates the response of the participant, which is weighted in accordance with the evaluation of the participant by the evaluation unit.

18. The information processing apparatus according to claim 16,
    wherein the aggregation unit aggregates responses for each type of the gathering.

19. The information processing apparatus according to claim 16, further comprising:
    a determination unit that determines a gathering in which activity degrees of the plurality of participants participating in the gathering satisfy a defined condition, among a plurality of gatherings,
    wherein the aggregation unit aggregates responses of the participants participating in the gathering, for each gathering determined by the determination unit.

20. The information processing apparatus according to claim 19,
   wherein the determination unit determines the gathering in accordance with similarity between the activity degrees of the plurality of participants.

* * * * *